United States Patent
Thompson et al.

(10) Patent No.: US 7,101,508 B2
(45) Date of Patent: Sep. 5, 2006

(54) CHEMICAL ARRAY FABRICATION ERRORS

(75) Inventors: Allen C. Thompson, San Francisco, CA (US); William D. Fisher, San Jose, CA (US); Michael P. Caren, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 321 days.

(21) Appl. No.: 10/210,126

(22) Filed: Jul. 31, 2002

(65) Prior Publication Data

US 2004/0023223 A1   Feb. 5, 2004

(51) Int. Cl.
  *B32B 5/02* (2006.01)
  *G01N 15/06* (2006.01)
  *G01N 1/10* (2006.01)
  *B01L 3/02* (2006.01)
  *G06K 9/00* (2006.01)

(52) U.S. Cl. .......................... 422/67; 422/100; 422/63; 422/68.1; 422/82.05; 436/180; 382/149; 382/151; 382/287; 382/291

(58) Field of Classification Search ................ 422/100, 422/63, 67, 68.1, 82.05; 382/149, 151, 287, 382/291; 436/180
See application file for complete search history.

(56) References Cited

U.S. PATENT DOCUMENTS

| | | | |
|---|---|---|---|
| 5,508,200 A | | 4/1996 | Tiffany et al. |
| 5,721,435 A * | | 2/1998 | Troll ...................... 250/559.29 |
| 5,981,733 A | | 11/1999 | Gamble et al. |
| 6,001,309 A | | 12/1999 | Gamble et al. |
| 6,086,190 A * | | 7/2000 | Schantz et al. ............... 347/81 |
| 6,232,072 B1 * | | 5/2001 | Fisher ........................... 435/6 |
| 6,574,359 B1 * | | 6/2003 | Hance ........................ 382/149 |
| 6,637,853 B1 * | | 10/2003 | Ahne et al. .................... 347/19 |
| 6,656,740 B1 * | | 12/2003 | Caren et al. ................ 436/164 |
| 6,673,315 B1 * | | 1/2004 | Sheridan et al. .............. 422/50 |

(Continued)

FOREIGN PATENT DOCUMENTS

GB    2355716 A    5/2001

(Continued)

*Primary Examiner*—Brian R. Gordon
(74) *Attorney, Agent, or Firm*—Gordon M. Stewart

(57) ABSTRACT

A method of fabricating an addressable array of chemical probes at respective feature locations on a substrate surface. The method may use a deposition apparatus with a substrate unit which includes the substrate and with a drop deposition unit which includes a drop deposition head. Such an apparatus when operated according to a target drive pattern based on nominal operating parameters of the apparatus provides the probes on the substrate surface in the target array pattern. The method may include depositing at least one drop from the head unit onto the substrate surface. A fiducial on the substrate unit is optionally viewed from a sensor. A deposited drop on the substrate surface is viewed from a sensor. An actual position of the viewed deposited drop may be determined relative to a fiducial on the substrate unit, based on the views of the fiducial and deposited drop. An error is determined based on any difference between the actual and target positions. Alternatively, an error for one or more deposition units may be determined based on a statistical difference between the actual and target positions of a set of multiple drops deposited from each deposition unit. The deposition apparatus is operated to deposit further drops from the head unit onto the substrate surface at feature locations while moving at least one of the substrate unit or head unit with respect to the other, so as to fabricate the array. Apparatus and computer program products are also provided.

11 Claims, 7 Drawing Sheets

U.S. PATENT DOCUMENTS

| | | | |
|---|---|---|---|
| 6,674,890 B1* | 1/2004 | Maeda et al. | 382/149 |
| 6,681,038 B1* | 1/2004 | Vilella | 382/145 |
| 6,689,319 B1* | 2/2004 | Fisher et al. | 422/67 |
| 6,710,798 B1* | 3/2004 | Hershel et al. | 348/87 |
| 6,738,505 B1* | 5/2004 | Prince | 382/150 |
| 6,738,820 B1* | 5/2004 | Hilt | 709/229 |
| 6,749,776 B1* | 6/2004 | Han et al. | 252/518.1 |
| 6,756,202 B1* | 6/2004 | Dorsel et al. | 435/6 |
| 6,863,755 B1* | 3/2005 | Nedblake et al. | 156/64 |
| 6,890,760 B1* | 5/2005 | Webb | 436/180 |
| 2003/0143551 A1* | 7/2003 | Cattell | 435/6 |
| 2003/0161761 A1* | 8/2003 | Williams et al. | 422/63 |
| 2004/0039532 A1* | 2/2004 | Bass | 702/19 |
| 2004/0048173 A1* | 3/2004 | Tutt et al. | 430/22 |
| 2004/0082059 A1* | 4/2004 | Webb et al. | 435/287.2 |
| 2005/0073539 A1* | 4/2005 | McGarry et al. | 347/14 |
| 2005/0163659 A1* | 7/2005 | Duvenneck et al. | 422/61 |

FOREIGN PATENT DOCUMENTS

| | | |
|---|---|---|
| WO | WO 98/41531 | 9/1998 |
| WO | WO 00/60425 | 10/2000 |

* cited by examiner

CHEMICAL ARRAY FABRICATION ERRORS

FIELD OF THE INVENTION

This invention relates to chemical arrays, such as polynucleotide or other biopolymer arrays (for example, DNA arrays), which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample. Biopolymer arrays can be fabricated by depositing previously obtained biopolymers (such as from synthesis or natural sources) onto a substrate, or by in situ synthesis methods. Methods of depositing obtained biopolymers include dispensing droplets to a substrate from dispensers such as pin or capillaries (such as described in U.S. Pat. No. 5,807,522) or such as pulse jets (such as a piezoelectric inkjet head, as described in PCT publications WO 95/25116 and WO 98/41531, and elsewhere). The substrate is coated with a suitable linking layer prior to deposition, such as with polylysine or other suitable coatings as described, for example, in U.S. Pat. No. 6,077,674 and the references cited therein.

For in situ fabrication methods, multiple different reagent droplets are deposited from drop dispensers at a given target location in order to form the final feature (hence a probe of the feature is synthesized on the array substrate). The in situ fabrication methods include those described in U.S. Pat. No. 5,449,754 for synthesizing peptide arrays, and described in WO 98/41531 and the references cited therein for polynucleotides. The in situ method for fabricating a polynucleotide array typically follows, at each of the multiple different addresses at which features are to be formed, the same conventional iterative sequence used in forming polynucleotides from nucleoside reagents on a support by means of known chemistry. This iterative sequence is as follows: (a) coupling a selected nucleoside through a phosphite linkage to a functionalized support in the first iteration, or a nucleoside bound to the substrate (i.e. the nucleoside-modified substrate) in subsequent iterations; (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in a known manner. As can be seen, in situ fabrication involves multiple cycles, whereas the deposition of previously obtained biopolymers is generally one cycle (that is, only one occurrence of probes occurs at each feature).

The foregoing chemistry of the synthesis of polynucleotides is described in detail, for example, in Caruthers, *Science* 230: 281–285, 1985; Itakura et al., *Ann. Rev. Biochem.* 53: 323–356; Hunkapillar et al., *Nature* 310: 105–110, 1984; and in "Synthesis of Oligonucleotide Derivatives in Design and Targeted Reaction of Oligonucleotide Derivatives", CRC Press, Boca Raton, Fla., pages 100 et seq., U.S. Pat. No. 4,458,066, U.S. Pat. No. 4,500,707, U.S. Pat. No. 5,153,319, U.S. Pat. No. 5,869,643, EP 0294196, and elsewhere. Suitable linking layers on the substrate include those as described in U.S. Pat. Nos. 6,235,488 and 6,258,454 and the references cited therein.

Further details of fabricating biopolymer arrays by depositing either previously obtained biopolymers or by the in situ method are disclosed in U.S. Pat. No. 6,242,266, U.S. Pat. No. 6,232,072, U.S. Pat. No. 6,180,351, and U.S. Pat. No. 6,171,797.

In array fabrication, the quantities of DNA available for the array are usually very small and expensive. Sample quantities available for testing are usually also very small and it is therefore desirable to simultaneously test the same sample against a large number of different probes on an array. These conditions require use of arrays with large numbers of very small, closely spaced features. It is important in such arrays that features actually be present, that they are put down accurately in the desired pattern, are of the correct size, and that the DNA is uniformly coated within the feature. Normally, in an automated apparatus the features are deposited according to a target array pattern. A target drive pattern is created from the target array pattern, which target drive pattern contains the instructions for driving the various components so as to provide the probes on the substrate in the target array pattern. The target drive pattern is created on the assumption that all components of the deposition apparatus are in their expected or normal ("nominal") positions and operating according to nominal parameters.

However, components in an array deposition apparatus each are subject to variances in its parameters within, or sometimes even outside of, normal tolerances for such component. For example, a dispensing head used to dispense fluid droplets to form the array, may have jets which vary slightly in the size of the droplets dispensed, the orientation of the jets with respect to one another, or the orientation of the head itself in the apparatus may be slightly off from a nominal position. While such variances can be reduced by constructing a dispensing apparatus with components of higher tolerance (that is, less variation), this can increase cost. Furthermore, while a given set of parameters may exist during manufacture of a given batch of arrays, these parameters may change over time, for example due to thermal expansion of a component. These effects result in use of the target drive pattern not producing the target array on the substrate. That is, there is a discrepancy between the target array pattern and the actual array pattern deposited. Such discrepancy may include mislocation of features, or features not being of the correct size. These discrepancies can occur in each cycle of the in situ process, or during deposition of presynthesized polynucleotides.

Errors of the foregoing type can be monitored and corrected to extent by detecting the positions of deposited drops and calculating their positions based on encoder information which provides feedback on component positions (such as the position of the head). However, the present invention realizes that while such a procedure can be highly useful it can have limitations. For example, encoder errors may vary over time. Also, these or other drop deposition errors may be non-linear (that is their magnitude may vary with the position of a drop deposition head relative to the substrate). Such further minor positioning errors may not be significant in typical sized substrates onto which multiple arrays are fabricated. However, the present invention further realizes that to increase manufacturing throughput substrate size should be increased to increase the number of arrays that can be simultaneously fabricated on the substrate, and that in such event errors of the foregoing type become more significant (primarily due to the longer distance of travel of the deposition head relative to the substrate).

It would be useful then, to provide a means by which arrays can be fabricated with an actual array pattern which is very close to the target array pattern. It would also be useful if such means was relatively reliable and easy to implement.

SUMMARY OF THE INVENTION

The present invention then, provides in one aspect a method of fabricating an addressable array of chemical probes at respective feature locations on a substrate surface. The method may use a deposition apparatus with a substrate unit which includes the substrate, and with a drop deposition unit which includes a drop deposition head. Such an apparatus may, when operated according to a target drive pattern based on nominal operating parameters of the apparatus, provide the probes on the substrate surface in the target array pattern. The method includes depositing at least one drop (and possibly multiple drops, for example at different locations on the substrate surface) from the head unit onto the substrate surface. Such drops may be referenced as "test drops" although they may or may not be part of the actual array to be fabricated. One or more fiducials on one of the substrate unit or head unit are viewed from a sensor on the other unit. One or more deposited drops is viewed on the substrate surface from a sensor (which may, for example, be on the head unit and which may be the same sensor used to view the one or more fiducials). For example, the one or more drops may be viewed in a same image captured by a same sensor (or alternatively, multiple sensors which move in unison on the head unit). An actual position of one or more viewed deposited drops relative to one or more of the viewed fiducials on the substrate unit is determined, based on the views of the one or more fiducials and the one or more deposited drops. An error is determined based on any difference between the actual and target positions. The deposition apparatus may be operated to deposit further drops from the head unit onto the substrate surface at feature locations while moving at least one of the substrate unit or head unit with respect to the other, so as to fabricate the array.

In another aspect of the present invention, a method is provided for fabricating an addressable array using an apparatus such as that already described. In this aspect, a set of multiple drops is deposited from at least one drop deposition unit (and, optionally, from each of multiple drop deposition units) in the head onto the substrate surface. An actual position of each of the deposited drops is deteremined (such as by viewing the deposited drops on the surface or otherwise determining the location of deposited drops, or by viewing deposited drop trajectories). An error based on a statistical difference (such as an average difference) between the actual and target positions is determined. The deposition apparatus is operated to deposit further drops from the head unit onto the substrate surface at feature locations while moving at least one of the substrate unit or head unit with respect to the other, so as to fabricate the array. Multiple drops may be deposited at different locations on the substrate surface. These multiple drops may be viewed and an actual position of the viewed deposited drops relative to one or more fiducials on the substrate unit determined based on those views. The error may be determined based on an average difference between the actual and target positions. "Average" in this context is used to refer to any single value that generally represents a set of values, and includes the mean, median, and norm.

In any aspect or embodiment of the present invention, the detected error can be used for various purposes. For example, a corrected drive pattern different from the target drive pattern can be derived based on the error, such that use of the corrected drive pattern results in a reduced discrepancy between the target and actual array patterns. Or, the firing of each printhead or nozzle may be timed so as to correct for the detected error. Or the printheads heads may be automatically adjusted with the use of computer-controlled actuators. The deposition apparatus may be operated according to the corrected drive pattern so as to fabricate the array. Alternatively, the actual positions of the further deposited drops deposited and viewed may be determined based on the views of those further drops and the determined error. The determined actual positions may be saved to a memory. In another use the method may be repeated for multiple arrays on one or more substrates, and the repetitions are halted or an operator alert activated when the error exceeds a predetermined limit. In a still further use a check (or adjustment) of one or more components of the apparatus may be performed (either automatically, or manually such as following an alert to the operator) when the error exceeds a predetermined limit or, in the case where the error is based on a statistical difference, where the variation in actual positions within the set deposited from a deposition unit exceeds a predetermined value.

The drops deposited so as to form the array may contain the chemical probes themselves or precursor units for the chemical probes at the different features (such as monomer containing drops when the probes are polymers, for example biomonomers used in the in situ synthesis method). In the second situation, the operating of the deposition apparatus to deposit the further drops may be repeated for each of multiple deposition cycles.

The present invention further provides an apparatus for fabricating an addressable array, as already described. The apparatus may include a substrate unit which comprises a substrate holder and optionally a substrate received on the holder, and a drop deposition unit which includes a drop deposition head. Such apparatus further includes a transport system to move the deposition unit with respect to a received substrate, and a sensor (for example, on the drop deposition unit), as well as a control unit. The control unit causes the apparatus to execute a method of the present invention.

The present invention further provides a computer program product which can be used to execute a method of the present invention, for example by executing the method on an apparatus of the present invention. This computer program product includes a computer readable storage medium having a computer program stored on it which, when loaded into a computer, instructs the processor to execute a method of the present invention.

The present invention then, including methods, apparatus, and computer program products thereof, can provide any one or more, of a number of useful benefits. For example, arrays can be fabricated with an actual array pattern which is very close to the target array pattern. Further, the invention is relatively reliable and easy to implement.

BRIEF DESCRIPTION OF THE DRAWINGS

To facilitate understanding, identical reference numerals have been used, where practical, to designate identical elements that are common to the Figures. Drawings are not to scale unless otherwise indicated.

DETAILED DESCRIPTION OF EMBODIMENTS OF THE INVENTION

Figure 1:
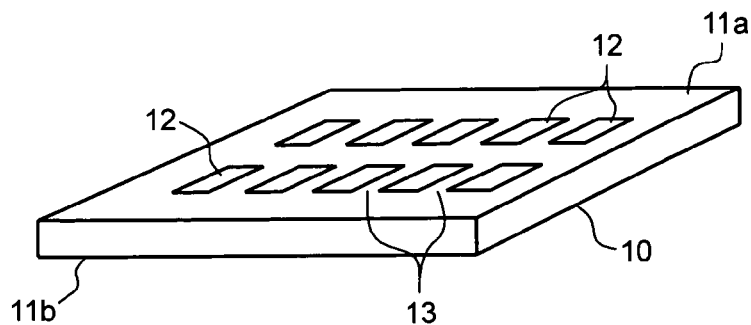
FIG. 1 is a perspective view of a substrate bearing multiple arrays, as may be produced by a method and apparatus of the present invention.

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A "peptide" is used to refer to an amino acid multimer of any length (for example, more than 1, 10 to 100, or more amino acid units). A biomonomer fluid or biopolymer fluid refers to a liquid containing either a biomonomer or biopolymer, respectively (typically in solution).

A "pulse jet" is a device which can dispense drops in the formation of an array. Pulse jets operate by delivering a pulse of pressure (such as by a piezoelectric or thermoelectric element) to liquid adjacent an outlet or orifice such that a drop will be dispensed therefrom. When the arrangement, selection, and movement of "dispensers" is referenced herein, it will be understood that this refers to the point from which drops are dispensed from the dispensers (such as the outlet orifices of pulse jets). A "drop" in reference to the dispensed liquid does not imply any particular shape, for example a "drop" dispensed by a pulse jet only refers to the volume (usually less than about 1000 pL) dispensed on a single activation. A drop which has contacted a substrate is often referred to as a "deposited drop" or the like, although sometimes it will be simply referenced as a drop when it is understood that it was previously deposited. An array feature may be formed from one or multiple pulses from one or multiple nozzles. Reference to "viewing" indicates observation by any optical device which can image all or a portion of an object, such as a 2-D or linescan camera or a raster scanning point light source and associated detector.

When a "spot" or "drop" is referenced, this may reference either a dried spot on the substrate resulting from drying of one or more deposited drops, or a wet spot on the substrate resulting from one or more deposited drops which have not yet dried. The head or substrate moving "as" or "while" droplets are dispensed includes actual movement during and/or between the dispensing of multiple droplets.

An "array", unless a contrary intention appears, includes any one, two or three dimensional arrangement of addressable regions bearing a particular chemical moiety to moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces.

In the case of an array, the "target" will be referenced as a moiety in a mobile phase (typically fluid), to be detected by probes ("target probes") which are bound to the substrate at the various regions. However, either of the "target" or "target probes" may be the one which is evaluated by the other (thus, either one could be an unknown mixture of polynucleotides to be evaluated by binding with the other). An "array layout" refers collectively to one or more characteristics of the features, such as feature positioning, one or more feature dimensions, and some indication of a moiety at a given location. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

It will also be appreciated that throughout the present application, that words such as "top", "upper", and "lower" are used in a relative sense only. "Fluid" is used herein 30 to reference a liquid. Reference to a singular item, includes the possibility that there are plural of the same items present. Furthermore, when one thing is "moved", "moving", "repositioned", "scanned", or the like, with respect to another, this implies relative motion only such that either thing or both might actually be moved in relation to the other. For example, when dispensers are "moved" relative to a substrate, either one of the dispensers or substrate may actually be put into motion by the transport system while the other is held still, or both may be put into motion. When one thing is determined "based on" another, this includes the possibility that the determination is solely from the other or from the other in combination with further data. "May" means optionally.

All patents and other cited references herein, are incorporated into this application by reference except insofar as any may conflict with the present application (in which case the present application prevails). Any method can be executed in the sequence to written or any other sequence where such is logically possible.

Figure 2:
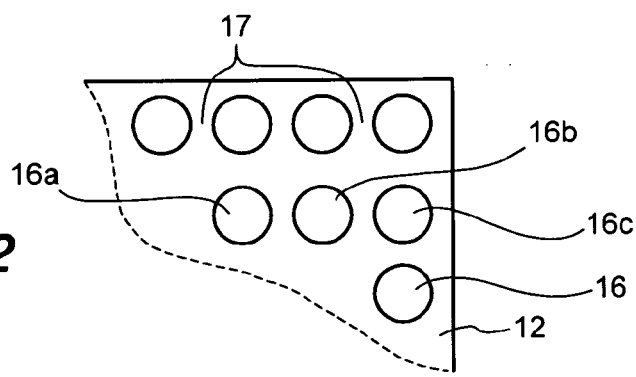
FIG. 2 is an enlarged view of a portion of FIG. 1 showing some of the identifiable individual regions (or "features") of a single array of FIG. 1.
Figure 3:
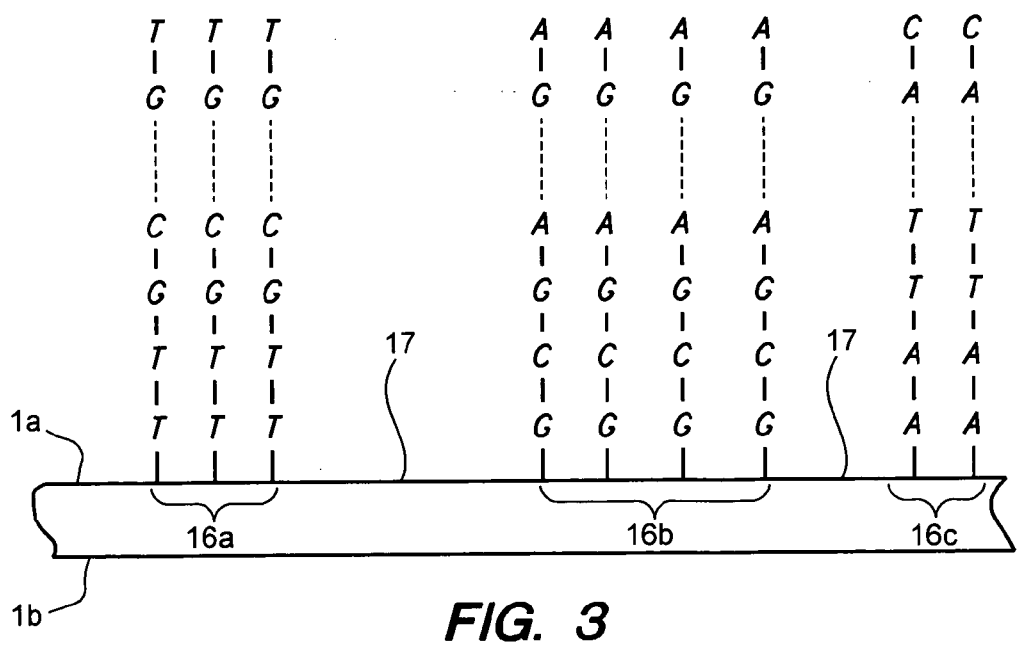
FIG. 3 is an enlarged cross-section of a portion of FIG. 2.

Referring first to FIGS. 1–3, typically methods and apparatus of the present invention produce a contiguous planar substrate 10 carrying one or more arrays 12 disposed across a front surface 11a of substrate 10 and separated by interarray areas 13. A back side 11b of substrate 10 does not carry any arrays 12. The arrays on substrate 10 can be designed for testing against any type of sample, whether a trial sample, reference sample, a combination of them, or a known mixture of polynucleotides (in which latter case the arrays may be composed of features carrying unknown sequences to be evaluated). While ten arrays 12 are shown in FIG. 1 and the different embodiments described below may use substrates with particular numbers of arrays, it will be understood that substrate 10 and the embodiments to be used with it, may use any number of desired arrays 12. Similarly, substrate 10 may be of any shape, and any apparatus used with it adapted accordingly. Depending upon intended use, any or all of arrays 12 may be the same or different from one another and each will contain multiple spots or features 16 of biopolymers in the form of polynucleotides. A typical array may contain from more than ten, more than one hundred, more than one thousand or ten thousand features, or even more than from one hundred thousand features. All of the features 16 may be different, or some could be the same (for example, when any repeats of each feature composition are excluded the remaining features may account for at least 5%, 10%, 20%, or 50% of the total number of features). In the case where arrays 12 are formed by the conventional in situ or deposition of previously obtained moieties, as described above, by depositing for each feature a droplet of reagent in each cycle such as by using a pulse jet such as an inkjet type head, interfeature areas 17 will typically be present which do not carry any polynucleotide. It will be appreciated though, that the interfeature areas 17, when present, could be of various sizes and configurations. Each feature carries a predetermined polynucleotide (which includes the possibility of mixtures of polynucleotides). As per usual, A, C, G, T represent the usual nucleotides. It will be understood that there may be a linker molecule (not shown) of any known types between the front surface 11a and the first nucleotide.

Features 16 can have widths (that is, diameter, for a round spot) in the range from a minimum of about 10 µm to a maximum of about 1.0 cm. In embodiments where very small spot sizes or feature sizes are desired, material can be deposited according to the invention in small spots whose width is in the range about 1.0 µm to 1.0 mm, usually about 5.0 µm to 500 µm, and more usually about 10 µm to 200 µm. Spot sizes can be adjusted as desired, by using one or a desired number of pulses from a pulse jet to provide the desired final spot size. Features which are not round may have areas equivalent to the area ranges of round features 16 resulting from the foregoing diameter ranges. The probes of features 16 are typically linked to substrate 10 through a suitable linker, not shown.

Each array 12 may cover an area of less than 100 cm$^2$, or even less than 50, 10 or 1 cm$^2$. In many embodiments, substrate 10 will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 2 cm, 1 cm, 5.0 mm, or even less than 0.5 mm, and usually more than 0.1 mm and less than 2 mm and more usually more than 0.2 and less than 1 mm. However, larger substrates can be used, particularly when such are cut after fabrication into smaller size substrates carrying a smaller total number of arrays 12. In the situation where the array is read by detecting fluorescence, substrate 10 may be of a material that emits low fluorescence upon illumination with the excitation light. Additionally, in this situation, substrate 10 may be transparent to reduce the absorption of incident illuminating laser light during reading of the array, and subsequent heating if the focused laser beam travels too slowly over a region.

FIGS. 2 and 3 illustrate an ideal array where actual features 16 are the same as the target (or desired) features, with each feature 16 being uniform in shape, size and composition, and the features 16 being regularly and correctly spaced. Such an array when fabricated by drop deposition methods, would require all reagent droplets for each feature to be uniform in shape and accurately deposited at the target feature location. In practice, such an ideal result is difficult to obtain due to fixed and random errors during fabrication.

Figure 4:
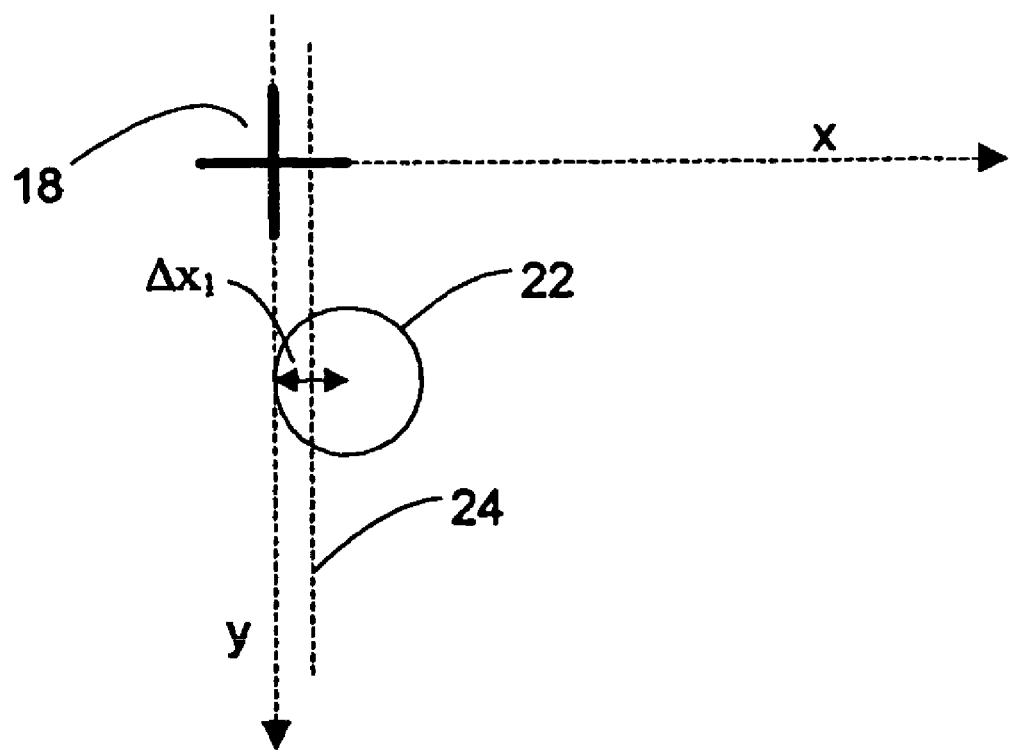
FIG. 4 illustrates operation of an embodiment of the present invention.

FIG. 4 illustrates an actual view of both a fiducial 18 and a deposited drop on surface 11a. Such an actual view may be obtained from a sensor in the form of camera 304 in a head unit of a deposition apparatus (see FIG. 8 and the accompanying description below). Based on the view, the actual position of the viewed deposited drop 22 relative to fiducial 18 can be determined (simply by viewing their relative positions in FIG. 4). An error in deposited drop 22 position in FIG. 4 can be determined based on the difference between the so determined actual position and the target position. For example, if the deposited drop 22 in FIG. 4 had a target position of the same y coordinate as the actual position of the deposited drop, but centered on the y axis, this would represent a determined displacement error $\Delta \times 1$ in FIG. 4. In FIG. 4 the deposited drop 22 and fiducial 18 are viewed in a same image captured by camera 304. By the "same image" in this context means what is captured without relative movement of the head unit and substrate unit, and it is sufficient that only a portion of the fiducial 18 and deposited drop 22 be captured in the same image. For example, in FIG. 8 camera 304 may be a linescan camera which moves in unison with the head unit in the x axis direction, and captures as an image only a single line 24 without the foregoing relative movement. In this case a portion of fiducial 18 and deposited drop 22 lying along line 24 are viewed in the same image. However, multiple such adjacent lines can be used to form a composite view of the entire FIG. 4. Also, it will be appreciated that a two-dimensional array sensor, such as a CCD sensor may be used instead of a linescan camera. In such case, the entire view in FIG. 4 may be viewed in one image. Viewing a fiducial 18 and a deposited drop 22 in a same image can provide the advantage that the error can be determined without relative movement of head and substrate units. As a result the error can be determined without introducing some unknown displacement error resulting from such relative movement.

One difficulty with the method in FIG. 4 occurs when camera 304 is incapable of viewing a fiducial and deposited drop in a same image (such as when camera 304 is a linescan camera capturing only one line at a time which is parallel to the y axis). In this situation, since camera 304 moves in unison with the head unit it will not be possible to determine an actual position of a deposited drop from a composite image assembled from multiple adjacent captured lines of a single fiducial and the single deposited drop. For example, an error may be present in the movement of the head unit (that is, the actual position of the head unit does not match a target position to which it is commanded to move). While counts from encoders 30, 34 (see FIG. 8) could be used in an attempt to determine the actual drop positions based on the encoder determined position of head unit, this procedure would not account for any errors in the encoders themselves or errors in determining the location of the camera image relative to the substrate. Thus the image of the drop and the fiducial together is more accurate in determining the location of the droplet on the substrate, because it is more direct.

Figure 5:
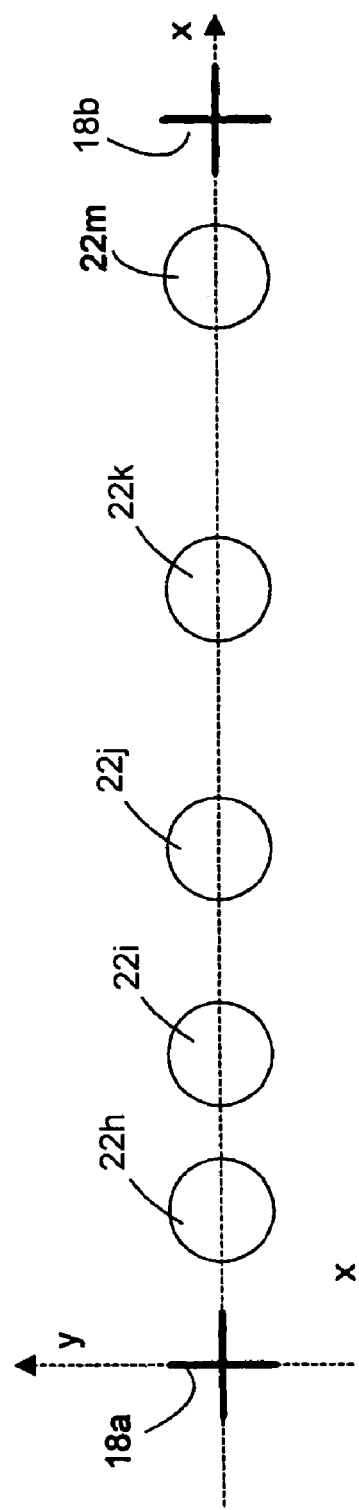
FIG. 5 illustrates operation of another embodiment of the present invention.

The arrangement in FIG. 5 illustrates operation of another embodiment of the present invention which can be used in the foregoing situation. FIG. 5 shows an actual view onto substrate surface 11a (see FIG. 1) which has multiple fiducials 18a, 18b and multiple deposited drops 22h through 22m deposited by the head unit of FIG. 8 as it moves along the x axis from left to right as viewed in FIG. 5. If the target positions of deposited drops 22h through 22m are such that they should be equally spaced, then it is apparent from FIG. 5 that there is a non-constant x position error which increases with increasing x axis displacement. However, if a composite view was formed from a linescan camera as camera 304 in FIG. 8, where each image captured by the sensor is a single line of pixels parallel to the y axis, this error could not be detected from viewing the multiple deposited drops 22h through 22m and fiducial 18a only. This is since camera 304 would be subject to many of the same positioning errors, and some different errors, as the deposited drops. However, this error can be detected by also viewing a second fiducial 18b. In such a composite view the x distance between fiducial 18b and deposited drop 22m would appear to be less than expected. The difference between the foregoing apparent and expected differences can be divided by the number of drops between the fiducials 18a, 18b (five in FIG. 5) and this taken as an average x displacement error which inherently provides the actual position of the deposited drops 22h through 22m. Alternatively, a more accurate modeling of the x displacement error can be obtained by depositing still additional drops and viewing those additional deposited drops and additional fiducials, and constructing a displacement error model based on all the viewed deposited drops and fiducials. A non-linear model can be constructed when three or more fiducials 18 are viewed with multiple deposited drops 22.

Figure 6:
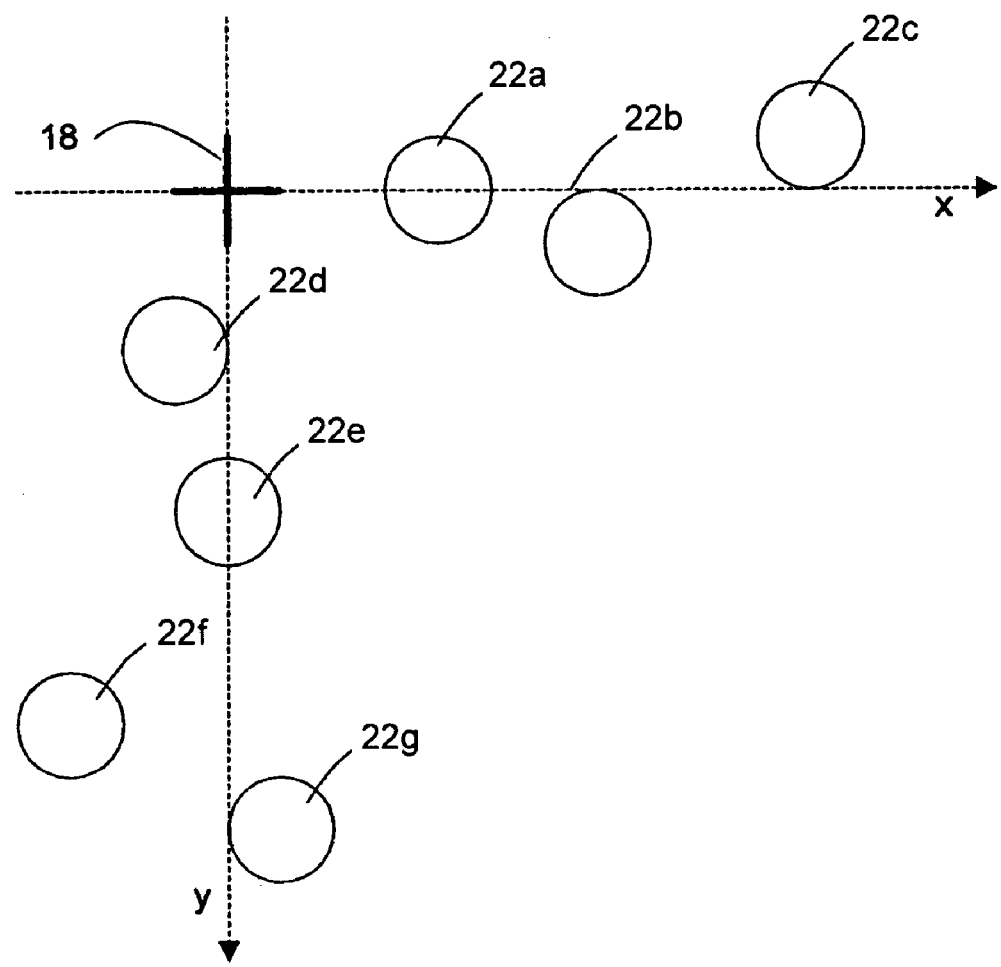
FIG. 6 illustrates operation of a further embodiment of the present invention.

Another method of determining the error is based on any average difference between the actual and target positions of multiple deposited drops at different locations on substrate surface 11a. Such a method is illustrated in FIG. 6, which shows a view of an actual drop deposition pattern on surface 11a of substrate 10. In FIG. 6 a set of deposited drops 22a through 22g is deposited with the same pulse jet nozzle (the nozzle to be evaluated) at target positions such that the center-to-center distance between any adjacent two is intended to be constant. Deposited drops 22a through 22c have target positions centered on the x axis, while deposited drops 22d through 22g have target positions centered on the y axis. A composite view of the actual deposited drops in FIG. 6 can be constructed from multiple lines of a linescan camera 304 which are parallel to the y axis. In depositing drops 22d through 22g there is no x axis displacement of the head unit with respect to the substrate, and there will be little such displacement in order to capture sufficient line images to view deposited drops 22d through 22g. However, there may be y axis displacement of both the head and camera 304. On the other hand, there is substantially more x axis displacement and little y axis displacement in depositing and viewing deposited drops 22a through 22c. Therefore, the average difference between the actual (FIG. 6 positions) and target positions (centered on the y axis) of deposited drops 22d through 22g can be determined as the x axis error of the nozzle being evaluated. The average difference between the actual (FIG. 6 positions) and target positions (centered on the x axis) of deposited drops 22a through 22c can be determined as the y axis error of the nozzle being evaluated. In general, the calculation of error based on statistical analysis of the droplet location relative to the substrate is more effective, since it will take into account the random nature of some of the errors. Examples of random errors include nozzle trajectory error and vibration error. If all the nozzles of a printhead are analyzed in this manner, a best statistical fit may be performed, and print trajectories and nozzle firing locations determined so as to produce an optimum total error.

Figure 7:
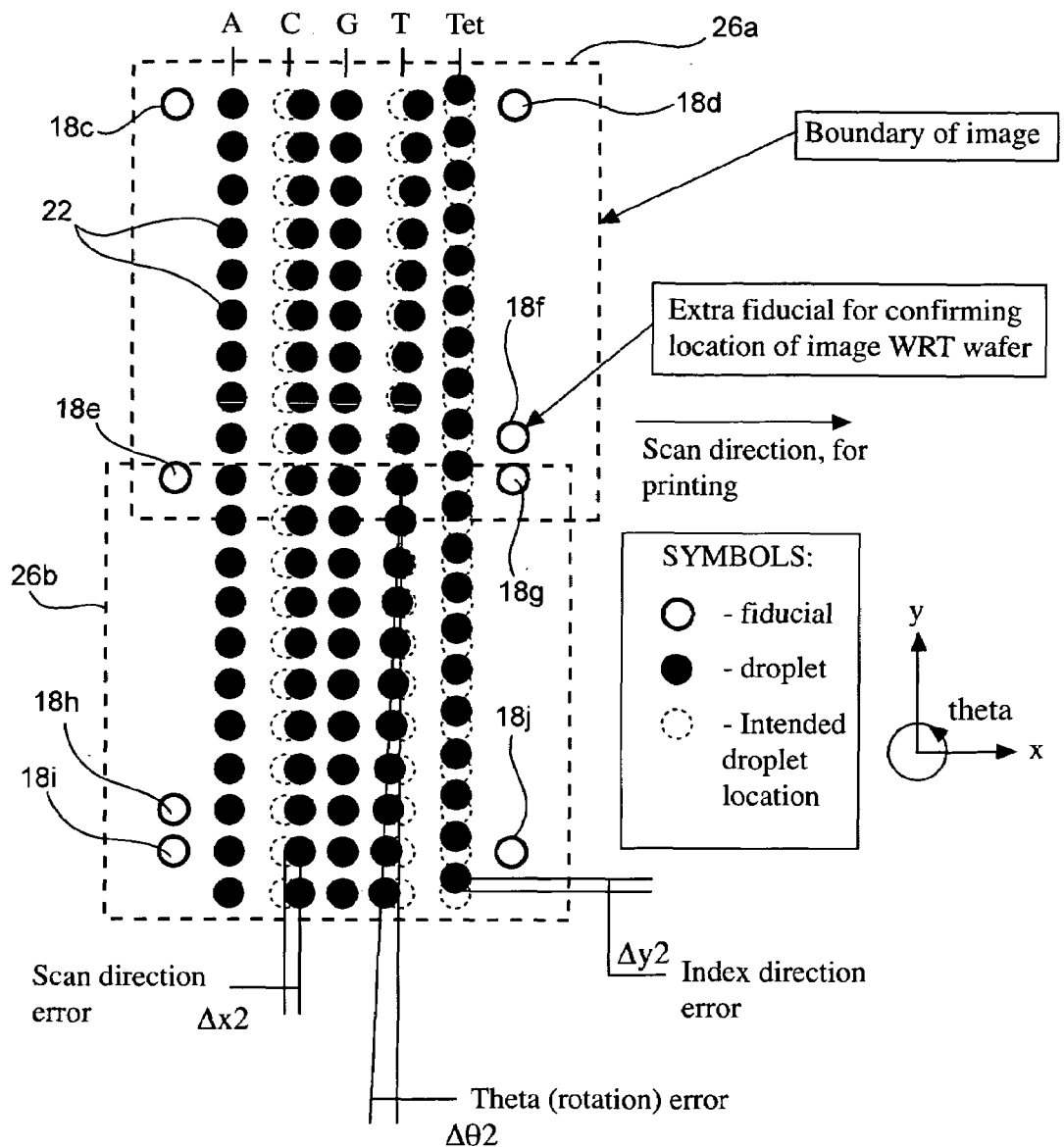
FIG. 7 illustrates a test pattern which may be deposited and viewed in the present invention.

FIG. 7 illustrates a test pattern of deposited drops 22 which may be viewed in addition to fiducials 18c through 18j on the substrate. An actual position of the viewed deposited drops 22 of the foregoing test pattern may be determined relative to one or more fiducials 18c through 18j on the substrate, in the manner described herein. The pattern of FIG. 7 may be delivered by depositing drops from all pulse jets of a head unit having four columns of pulse jets, each column with twenty members, while the head unit is held still with respect to a substrate (during actual array fabrication the head unit would normally be scanned in direction "x" and incremented one position in the "y" direction at the end of each line, in a raster fashion). The test pattern may be deposited between arrays 12 to be fabricated on the same substrate as the test pattern, the fiducials 18 having been previously provided on the substrate surface 11a. In FIG. 7 the solid circles represent deposited droplets, the hollow circles (unbroken lines) fiducials 18c-18j, and the hollow circles of broken lines represent target locations for deposited drops. Each column delivered one phosphoramidite monomer (A, C, G, or T) or phosphoramidite activator (T), in a known manner in polynucleotide in situ synthesis. Some of the errors which may occur during drop deposition are further illustrated in FIG. 7, and include displacement errors $\Delta x2$ and $\Delta y2$, as well as a rotation error $\Delta\theta 2$.

Note that in FIG. 7 fiducials 18c-18j each have a same size and same shape to the deposited drops 22 (in FIG. 7, both are circular and have a same area). However, a test drop and fiducial being the "same size" includes the possibility of one of them being at least 50%, at least 75%, at least 90%, or at least 95% the area of the other. This facilitates viewing fiducials 18c-18j and deposited drops 22 with a same camera (although different cameras could be used). Further multiple fiducials 18c, 18e, 18h, 18j (or 18c, 18d) are deposited in a same pattern as the test drops (in FIG. 7, both lie along straight lines). This permits use of a same algorithm in determining the location of deposited drops and fiducials. In the event that multiple images 26a, 26b must be captured in order to view the entire deposited test pattern (each image including different deposited drops in the pattern, although some may be the same in each image), it is helpful to have the same fiducials 18e, 18g included in the different images 26a, 26b to assist in correctly stitching the image data together from the multiple images 26a, 26b. Also, having multiple fiducials 18c, 18e, 18h, 18i or 18d, 18f, 18g, 18j in a pattern (in the illustrated case, in a line) along the y direction can provide verification of substrate location, aid in stitching image data together from multiple images, and verify that encoder pulses have been read correctly. Note that in the foregoing stitching situations, the same advantage can be obtained where the captured images are other than area images illustrated in FIG. 7 (for example, where the images are line images from a linescan camera extending the "y" length of the first and second images 26a, 26b).

Figure 8:
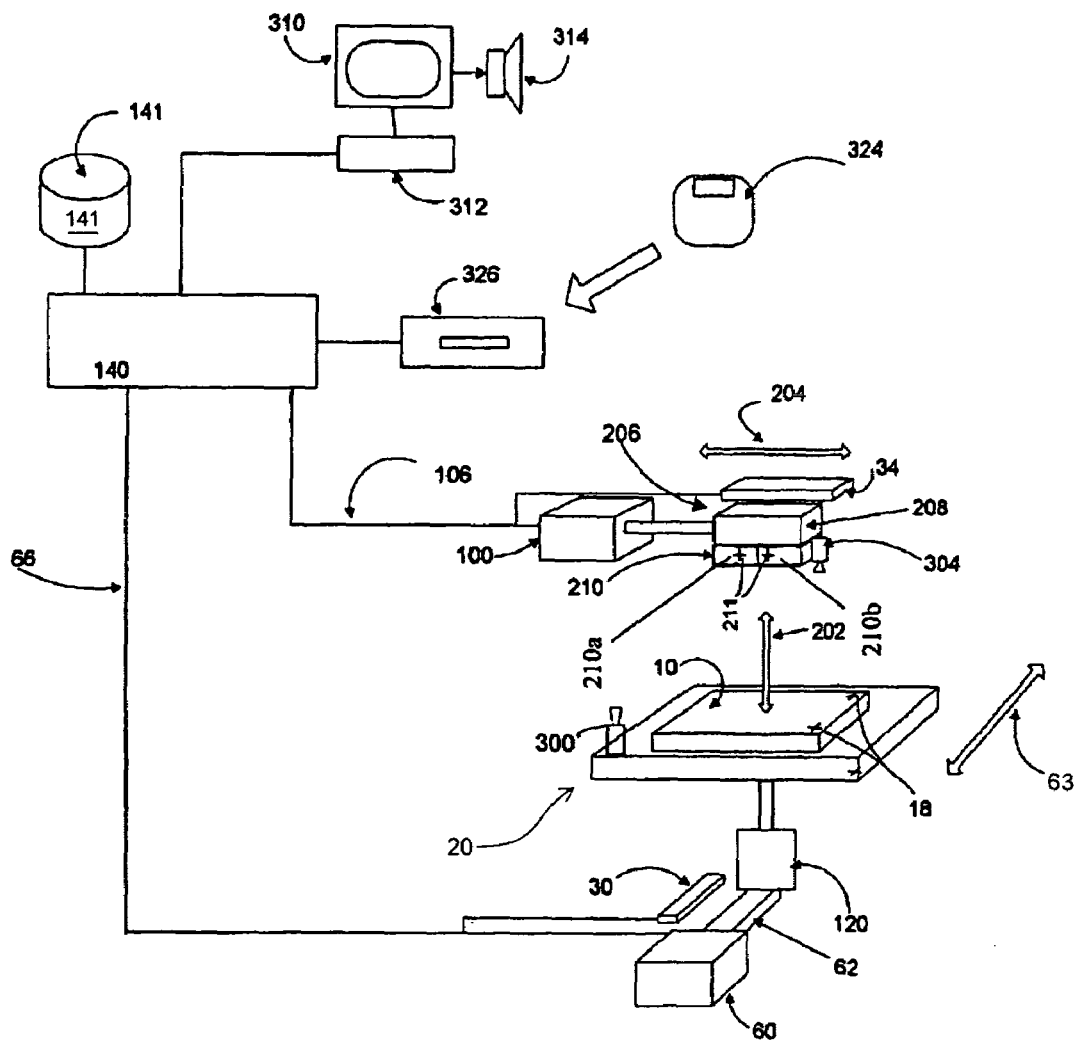
FIG. 8 is a schematic view of an apparatus of the present invention.

An apparatus which can execute a method of the present invention, and a method as executed by that apparatus using the above concepts, will now be described referring first to FIG. 8. Note that the apparatus schematically illustrated in FIG. 8 can be used to fabricate arrays 12 using the deposition of previously obtained biopolymers, or using the in situ fabrication method. The apparatus of the present invention which is shown in FIG. 8 includes a substrate station 20 on which can be mounted a substrate 10. Substrate station 20 with any components positioned or attached for movement in unison with substrate station 20 (for example, with mounted substrate 10) may be collectively referenced as a substrate unit. Pins or similar means (not shown) can be provided on substrate station 20 by which to approximately align substrate 10 to a nominal position thereon. Substrate station 20 can include a vacuum chuck connected to a suitable vacuum source (not shown) to retain a substrate 10 without exerting too much pressure thereon, since substrate 10 is often made of glass.

A dispensing head system 210, which includes two heads 210a and 210b, is retained by a head retainer 208. Head system 210 and any components (such as head retainer 208) positioned or attached with movement in unison with head system 210, may be collectively referenced as a head unit. Head system 210 has fiducial markings 211, for purposes described below, and can be positioned at any position facing substrate 10 by means of a positioning system. The positioning system includes a carriage 62 connected to a first transporter 60 controlled by processor 140 through line 66, and a second transporter 100 controlled by processor 140 through line 106. Transporter 60 and carriage 62 are used execute one axis positioning of station 20 (and hence mounted substrate 10) facing the dispensing head 210, by moving it in the direction of nominal axis 63, while transporter 100 is used to provide adjustment of the position of head retainer 208 (and hence head 210) in a direction of nominal axis 204. In this manner, head 210 can be scanned line by line, by scanning along a line over substrate 10 in the direction of axis 204 using transporter 100, while line by line movement of substrate 10 in a direction of axis 63 is provided by transporter 60. Head 210 may also optionally be moved in a vertical direction 202, by another suitable transporter (not shown). However, it will be appreciated that other scanning configurations could be used. However, it will be appreciated that both transporters 60 and 100, or either one of them, with suitable construction, could be used to perform the foregoing scanning of head 210 with respect to substrate 10. Thus, when the present application refers to "positioning" one element (such as head 210) in relation to another element (such as one of the stations 20 or substrate 10) it will be understood that any required moving can be accomplished by moving either element or a combination of both of them. An encoder 30 communicates with processor 140 to provide data on the exact location of substrate station 20 (and hence substrate 10 if positioned correctly on substrate station 20), while encoder 34 provides data on the exact location of holder 208 (and hence head 210 if positioned correctly on holder 208). Any suitable encoder, such as an optical encoder, may be used which provides data on linear position.

Angular positioning of substrate station 20 is provided by a transporter 120, which can rotate substrate station 20 about axis 202 under control of processor 140. Typically, substrate station 20 (and hence a mounted substrate) is rotated by transporter 120 under control of processor 140 in response to an observed angular position of substrate 10 as determined by processor 140 through viewing one or more fiducial marks on substrate 10 (particularly fiducial marks 18) with camera 304. This rotation will continue until substrate 10 has reached a predetermined angular relationship with respect to dispensing head 210. In the case of a square or rectangular substrate, the mounted substrate 10 will typically be rotated to align one-edge (length or width) with the scan direction of head 210 along axis 204. Note that fiducial marks 18 can be deposited chromium adhering to surface 11a, or laser ablated marks, scratch marks, or other suitable marks in front surface 11a. Fiducial marks on a surface are generally positioned with a high degree of precision with respect to one another (such precision, for example, having an error which is less in magnitude than any typical expected error in the actual positioning of a deposited drop relative to the target position of that deposited drop).

Head 210 may be of a type commonly used in an ink jet type of printer and may, for example, have one hundred fifty drop dispensing orifices in each of two parallel rows, six chambers for holding polynucleotide solution communicating with the three hundred orifices, and three hundred ejectors which are positioned in the chambers opposite a corresponding orifice. Each ejector is in the form of an electrical resistor operating as a heating element under control of processor 140 (although piezoelectric elements could be used instead). Each orifice with its associated ejector and portion of the chamber, defines a corresponding pulse jet with the orifice acting as a nozzle. Thus, there are three hundred pulse jets in this configuration, although it will be appreciated that head 210 could, for example, have more or less pulse jets as desired (for example, at least ten or at least one hundred pulse jets). In this manner, application of a single electric pulse to an ejector causes a droplet to be dispensed from a corresponding orifice. In the foregoing configuration, typically about twenty orifices in each group of six reservoirs (many of the orifices are unused and are plugged with glue), will be dispensing the same fluid. Certain elements of the head 210 can be adapted from parts of a commercially available thermal inkjet print head device available from Hewlett-Packard Co. as part no. HP51645A. The foregoing head 210 and other suitable dispensing head designs are described in more detail in U.S. patent application entitled "A MULTIPLE RESERVOIR INK JET DEVICE FOR THE FABRICATION OF BIOMOLECULAR ARRAYS" Ser. No. 09/150,507 filed Sep. 9, 1998. However, other head configurations can be used, for example a head with thirty reservoirs, and even multiple heads can also be used as desired.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. The size of a final deposited drop can also be adjusted as desired, by using one or a desired number of pulses from a pulse jet. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The apparatus further includes a sensor in the form of a first camera 300 located to view fiducial markings on head 210 and/or the positions of the nozzles on head 210. Typical fiducial markings are shown as fiducial markings 211 on the side of head 210 for visibility, although in practice fiducial marks viewed by first camera 300 may be on the underside of head 210. A second sensor in the form of a second camera 304, is located to observe the positions of fiducial markings 18 on substrate. Cameras 300 and 304 communicate with processor 140, and each should have a resolution that provides a pixel size of about 1 to 100 micrometers and more typically about 4 to 20 micrometers or even 1 to 5 micrometers. Any suitable analog or digital image capture device (including a line by line scanner) can be used for such camera, although if an analog camera is used processor 140 should include a suitable analog/digital converter. Further, other numbers of cameras may be used. For example, a single camera with the correct orientation and parameters, could be used in place of cameras 300 and 304. A display 310, speaker 314, and operator input device 312, are further provided. Operator input device 312 may, for example, be a keyboard, mouse, or the like. Processor 140 has access to a memory 141, and controls print head 210 (specifically, the activation of the ejectors therein), operation of the positioning system, operation of each jet in print head 210, capture of images from the cameras, and operation display 310 and speaker 314. Memory 141 may be any suitable device in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the functions required of it as described below. It will be appreciated though, that when a "processor" such as processor 140 (which acts as a control unit of the apparatus) is referenced throughout this application, that such includes any hardware and/or software combination which will perform the required functions. A microprocessor which provides the target drive pattern, together with the foregoing programmed device, then operates as a "processor" of the present invention. The programming can be provided remotely to processor 140, or previously saved in a computer program product such as memory 141 or some other portable or fixed computer readable storage medium using any of those devices mentioned below in connection with memory 141. For example, a magnetic or optical disk 324 may carry the programming, and can be read by disk reader 326.

Operation of the apparatus of FIG. 8 in accordance with a method of the present invention, will now be described. First, it will be assumed that memory 141 holds a target drive pattern. This target drive pattern is the instructions for operating the apparatus components as required to form the target array (which includes target locations and dimension for each spot) on substrate 10 and includes, for example, movement commands to transporters 60 and 100 as well as firing commands for each of the pulse jets in head 210 coordinated with the movement of head 210 and substrate 10, as well as instructions for which polynucleotide solution (or precursor) is to be loaded in each pulse jet (that is, the "loading pattern"). This target drive pattern is based upon the target array pattern and can have either been input from an appropriate source (such as input device 312, a portable magnetic or optical medium, or from a remote server, any of which communicate with processor 140), or may have been determined by processor 140 based upon an input target array pattern (using any of the appropriate sources previously mentioned) and the previously known nominal operating parameters of the apparatus. Further, it will be assumed that drops of different biomonomer or biopolymer containing fluids (or other fluids) have been placed at respective regions of a loading station (not shown). Operation of the following sequences are controlled by processor 140, following initial operator activation, unless a contrary indication appears.

Substrate 10 is loaded onto substrate station 20 either manually by an operator, or optionally by a suitable automated driver (not shown) controlled, for example, by processor 140. For any given substrate 10, the operation is basically follows: (i) determine the target drive pattern (if not already provided) to obtain target array pattern, based on nominal operating parameters and target polynucleotide array pattern; (ii) deposit one or more drops (the "test drops") from one or more pulse jets in a test pattern onto the substrate surface (which test pattern may be positioned between arrays 12 to be fabricated on a given substrate 10);

(iii) view one or more fiducials and deposited drops on the substrate surface; (iv) determine the actual position of the one or more viewed drops relative to the one or more viewed fiducials on the substrate unit, based on the views of them; (v) determine an error based on any difference between the actual and target positions; (vi) operate the deposition apparatus to deposit further drops from the head unit onto the substrate surface at feature locations while moving at least one of the substrate unit and head with respect to the other, so as to fabricate the array. In the foregoing procedure any of the drop deposition patterns and error determinations as described above may be used. It will be appreciated that any discrepancy between a nominal parameter and an actual sensed parameter, may optionally only be classified as an "error" in an operating parameter, if it meets or exceeds a predetermined threshold value. The method will account for an error without a need to consider the source of the error (for example, Abbe errors, thermal expansion errors, nozzle trajectory errors, and the like).

As discussed above, the detected error can be used in a number of ways. In one embodiment a corrected drive pattern different from the target drive pattern can be derived, such that use of the corrected drive pattern results in a reduced discrepancy between the target and actual array patterns. The deposition apparatus can then be operated according to the corrected drive pattern to fabricate the array. Additionally, the corrected drive pattern may also be selected so as to reduce any difference in deposited location of the drops of a multiple drop set deposited for each feature (for example, the drops deposited during multiple cycles of in situ synthesis). That is, to better align the locations of the drops within such a multiple drop set. Alternatively, the error can be saved in a memory (such as memory 141 or a portable storage medium) or used to determine the actual positions of the viewed further drops deposited, and the actual positions saved in a memory (such as memory 141 or a portable storage medium) in association with a code associated with each array. The saved error or actual positions can be later retrieved at a user location based on the code associated with each array, and used to control reading of the array or interpret data read from the array. Such a technique for using array layout information is disclosed in detail in U.S. Pat. No. 6,180,351 incorporated herein by reference. The techniques of that patent are adapted simply by the user station retrieving the-actual positions as part of the array layout or the target array layout plus the saved error. In a further alternative, when the error exceeds a predetermined limit, any deposition (including further cycles) can be halted or an operator alert activated, or an automated or manual performance check or adjustment of one or more apparatus components performed (for example, in response to the operator alert). Any detected error can also be used in any of the ways as described in U.S. patent application Ser. Nos. 09/359527 and 09/302898, as well as Great Britain Patent Publication 2355716 (patent application number 0010489.3 filed Apr. 28, 2000).

Figure 9:
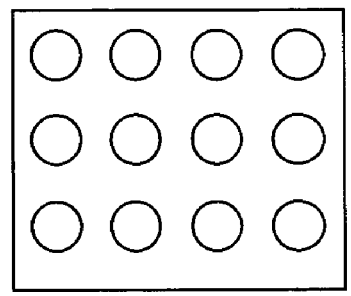
FIG. 9 illustrates a target drive pattern for an array to be fabricated.
Figure 10:
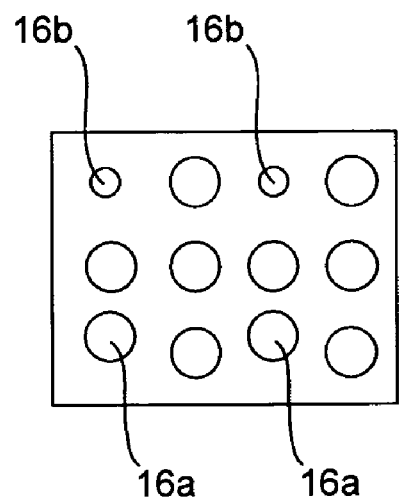
FIG. 10 illustrates an actual array pattern that might be obtained using the target drive pattern of FIG. 9.
Figure 11:
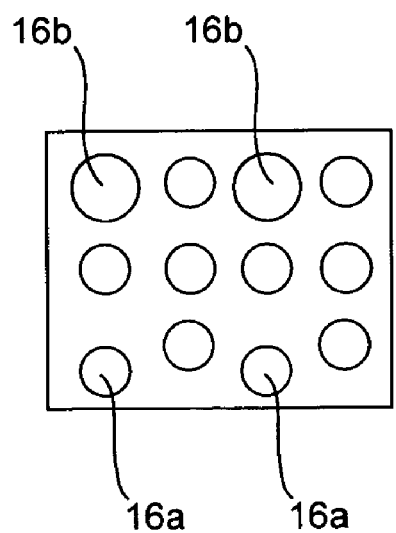
FIG. 11 illustrates a corrected drive pattern.

When a corrected a corrected drive pattern is derived by processor 140 a manner of correction can be more readily understood by reference to FIGS. 9 through 11. In particular, FIG. 8 represents an image in memory 141 of a portion of the target drive pattern. It will be assumed that this pattern is created by a dispensing head with a three by two matrix of dispensing jets (oriented with three jets in the vertical direction of FIGS. 9–11 and two in the horizontal direction), thus requiring a firing of all jets, followed by head displacement and another firing of all jets. Hence FIG. 8 corresponds to the appearance of the target array pattern if all relevant components of the deposition apparatus are operating according to their normal parameters ("operating" in this context includes correct positioning, whether static or dynamic). However, from viewing previous test prints by camera 304, processor 140 determines there is an error in relative orientation of the nozzle of head 210 which produces spots 16a. Similarly, an error is determined in fluid volumes deposited by the nozzle of head 210 which produces spots 16b. Processor 140 then derives a corrected drive pattern, the image in memory of the corrected drive pattern being illustrated in FIG. 8. This corrected drive pattern incorporates an inverse of the determined errors. That is, in order to correct for displacement (in the upward direction as viewed in FIG. 10) of spots 16a, the actual drive image will contain an instruction to move the head lower (as viewed in FIG. 11) than the nominal position of FIG. 8 to compensate for the displacement in FIG. 10. Similarly, to correct for the below expected volume (that is, the nominal volume) produced by the jets producing features 16b, the actual drive image will contain an instruction for that jet to fire multiple spots or with more energy (this appearing as enlarged features 16b in FIG. 11) to compensate for the low volume error. Alternatively, the actual drive image can be an instruction to switch to a different jet in the head when a deviation from nominal volume is encountered which may be more than a predetermined tolerance, and to compensate for the different position of the different jet accordingly. While the illustrated errors in FIG. 10 relate to individual spots, other errors can be general in that they relate to all spots. For example, an error in the position of substrate 10 on substrate station 20 is a general error, and the corrected drive pattern could be the same as the target drive pattern but with the addition of a set of offset instructions to the positioning system, such as a single instruction to one or any combination of transporters 60, 100, 120, to offset the position system from nominal to compensate for this error.

The apparatus is then operated as follows: (a) load head system 210 as needed with a first set of polynucleotide containing solutions or with their precursors such as phosphoramidites and an activator (for example, a given head may be able to hold n different members); (b) dispense droplets from head system 210 onto surface 11a of substrate 10, or onto a set of substrates in accordance with the target or corrected drive patterns for at least one array 12; and (c) repeat the foregoing sequence as needed starting at step (i) with a second set and subsequent sets of solutions for different features. In the case where an array is being fabricated by deposition of previously obtained polynucleotides, one cycle of the foregoing will complete fabrication of the array. In the case where the array is being fabricated by the in situ method, the foregoing procedure of depositing further drops to fabricate the array may be repeated for the same features in each of multiple cycles. Optionally, as another means of providing operating parameter data, the deposited arrays can be inspected by capturing one or more images such as from camera 304 and comparing the deposited array pattern with the target array pattern. Also, the depositing of one or more test drops, viewing one or more fiducials, viewing the one or more deposited drops, determining an actual position of the viewed deposited test drops, and determining an error, all as described above, may be repeated for each deposition cycle during the in situ method.

A loading sequence for head system 210 is more completely described in co-pending patent applications "FABRICATING BIOPOLYMER ARRAYS", by Caren et al., Ser. No. 09/302,922 filed Apr. 30, 1999 and assigned to the same assignee as the present application, and U.S. Pat. No.

6,242,266, and the references cited therein, including the possibility of using a flexible microtitre plate as described in U.S. patent application "Method and Apparatus for Liquid Transfer", Ser. No. 09/183,604. Those references and all other references cited in the present application, are incorporated into this application by reference. Processor 140 can control pressure within head 210 to load each polynucleotide solution into the chambers in the head by drawing it through the orifices.

During the dispensing of any drops processor 140 will operate the apparatus according to the target or corrected drive pattern (or test pattern), by causing the positioning system to position head 210 facing substrate station 20, and particularly the mounted substrate 10, and with head 210 at an appropriate distance from substrate 10. Processor 140 then causes the positioning system to scan head 210 across substrate 10 line by line (or in some other desired pattern), while coordinating activation of the ejectors in head 210 so as to dispense droplets in accordance with the target pattern.

At this point the droplet dispensing sequence is complete.

In an alternative to the above described embodiment the corrected drive pattern, instead of being derived prior to beginning deposition of droplets, may be created "on the fly". In one way of accomplishing this, the corrected drive pattern is created by modifying, based on the detected error, instructions to at least one deposition apparatus component which were based on the target drive pattern. This is done during the deposition of the probes or probe precursors. For example, the encoders 34 may be of a type which simply sends a pulse to the head at a certain spatial frequency; on each such pulse, the image file instructs the drive electronics which nozzles should be fired. Instead of deriving a corrected drive pattern in memory 141 so that the encoder pulses will cause accurate printing, the encoder signals may be processed by processor 140 to cause a non-distorted image to print accurately.

In one mode of operation an apparatus, method, or computer program of the present invention do not actually derive a target drive pattern from a target array pattern, but instead simply derive a corrected drive pattern from the target pattern, nominal conditions and detected error (when an error is detected). This can be done before fabrication of a given array has started at least when the error is detected before such fabrication has started (for example, as a result of determining an error from a previously deposited test pattern or another array), or during such fabrication. Again, the target drive pattern may be saved in memory or just derived during the actual array fabrication and sent as instructions directly to the apparatus components.

Following receipt by a user of an array made by an apparatus or method of the present invention, it will typically be exposed to a sample (for example, a fluorescently labeled polynucleotide or protein containing sample) and the array then read. Reading of the array may be accomplished by illuminating the array and reading the location and intensity of the resulting fluorescence at each feature of the array. For example, a scanner may be used for this purpose which is similar to the AGILENT MICROARRAY SCANNER manufactured by Agilent Technologies, Palo Alto, Calif. Other suitable apparatus and methods are described in U.S. patent applications Ser. No. 09/846125 "Reading Multi-Featured Arrays" by Dorsel et al.; and Ser. No. 09/430214 "Interrogating Multi-Featured Arrays" by Dorsel et al. As previously mentioned, these references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,251,685, U.S. Pat. No. 6,221,583 and elsewhere). A code associated with the array can be used to retrieve the array layout (target or actual) and any saved error, in the manner already mentioned. Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample, or whether or not a pattern indicates a particular condition of an organism from which the sample came). The results of the reading (processed or not) may be forwarded (such as by communication) to a remote location if desired, and received there for further use (such as further processing).

The present methods and apparatus may be used to deposit biopolymers or other chemical moieties on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc.

In the present invention, any of a variety of geometries of arrays on a substrate 10 may be fabricated other than the rectilinear rows and columns of arrays 12 of FIG. 1. For example, arrays 12 can be arranged in a sequence of curvilinear rows across the substrate surface (for example, a sequence of concentric circles or semi-circles of spots), or in some other arrangement. Similarly, the pattern of features 16 may be varied from the rectilinear rows and columns of spots in FIG. 2 to include, for example, a sequence of curvilinear rows across the substrate surface (for example, a sequence of concentric circles or semi-circles of spots), or some other regular pattern. Even irregular arrangements are possible provided a user is provided with some means (for example, an accompanying description) of the location and an identifying characteristic of the features (either before or after exposure to a sample). In any such cases, the arrangement of dispensers in head system 210 may be altered accordingly. The configuration of the arrays and their features may be selected according to manufacturing, handling, and use considerations.

As mentioned above, another aspect of a method of fabricating arrays of the present invention may or may not use the presence of fiducials as described above. In this aspect, a set of multiple drops may be deposited from at least one drop deposition unit (and, optionally, from each of multiple drop deposition units) in the head 210 onto the substrate surface 11*a*. An actual position of each of the deposited drops is deteremined (such as by viewing the deposited drops on the surface or otherwise determining the location of deposited drops, or by viewing deposited drop trajectories). An error based on a statistical difference (such as an average difference) between the actual and target positions is determined. The actual position and error determinations may be performed in the same manner as already described in connection with FIG. 6. Alternatively, some other method of determining the actual positions of deposited drops may be used (such as by viewing their trajectories or by using a different drop detection device rather than a camera). The deposition apparatus is operated to deposit further drops from the head unit onto the substrate surface at feature locations while moving at least one of the substrate unit or head unit with respect to the other, so as to fabricate the array. The detected error for each deposition unit (sometimes referenced as a "nozzle") can be used in the any of the manners described herein.

The substrates will typically be non-porous, and may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fused silica; plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties are deposited may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated).

Various modifications to the embodiments of the particular embodiments described above are, of course, possible. Accordingly, the present invention is not limited to the particular embodiments described in detail above.

What is claimed is:

1. An apparatus for fabricating an addressable array having multiple features carrying chemical probes at different locations on a substrate surface, which when operated according to a target drive pattern based on nominal operating parameters of the apparatus provides the probes on the substrate surface in a target array pattern, the apparatus comprising: a) a substrate unit which comprises a substrate holder and optionally a substrate received on the holder; b) a drop deposition unit which includes a drop deposition head; c) a transport system to move the deposition unit with respect to a received substrate; d) at least one sensor; e) a control unit which includes a processor programmed to operate the apparatus to: i) deposit at least one drop from the head unit onto a received substrate surface; ii) view a fiducial on the substrate unit from a sensor; iii) view a deposited drop on the substrate surface, from a sensor; iv) determine an actual position of the viewed deposited drop relative to a fiducial on the substrate unit, based on the views of the fiducial and deposited drop; v) determine an error based on any difference between the actual and target positions; vi) deposits further drops from the head unit onto the substrate surface at feature locations while moving at least one of the substrate unit or head unit with respect to the other, so as to fabricate the array.

2. An apparatus according to claim 1 wherein the sensors in (ii) and (iii) are on the drop deposition unit.

3. An apparatus according to claim 1 wherein the control unit operates the apparatus such that multiple fiducials are viewed in (ii), and an actual position of the viewed deposited drop is determined in (iv) relative to a fiducial based on the views of the multiple fiducials and the view of the deposited drop.

4. An apparatus according to claim 1 wherein the control unit operates the apparatus such that: multiple drops are deposited in (i) at different locations on the substrate surface which multiple drops are viewed in (iii); an actual position of the viewed deposited drops relative to a fiducial on the substrate unit is determined in (iv), based on the views of the fiducial and deposited drops; and the error is determined in (v) based on a statistical difference between the actual and target positions.

5. An apparatus according to claim 4 wherein the statistical difference is an average difference between the actual and target positions.

6. An apparatus according to claim 1 wherein the deposited drop and fiducial in (i) and (ii) are viewed in a same image captured by the same sensor.

7. An apparatus according to claim 1 wherein the control unit additionally: derives a corrected drive pattern when an error is detected, said corrected drive pattern being different from the target drive pattern such that use of the corrected drive pattern results in a reduced discrepancy between the target and actual array patterns; and wherein the deposition apparatus is operated in according to the corrected drive pattern so as to fabricate the array.

8. An apparatus according to claim 1 wherein the processor additionally: determines the actual positions of the further drops deposited and viewed in (vi) based on the views and the determined error; and saves the determined actual positions to a memory.

9. An apparatus according to claim 1 wherein said controller further generates an updated drive pattern based on said determination of error.

10. An apparatus according to claim 9 wherein said updating results in a corrected drive pattern.

11. An apparatus according to claim 10 wherein said correction of the drive pattern occurs while the drop deposition unit is depositing drops on the substrate surface.

* * * * *